US009339435B2

(12) United States Patent  
Kiremitci

(10) Patent No.: US 9,339,435 B2  
(45) Date of Patent: May 17, 2016

(54) PHOTO LIGHT THERAPY AND MASSAGING APPARATUS

(76) Inventor: Kirkor Kiremitci, Laval (CA)

( * ) Notice: Subject to any disclaimer, the term of this patent is extended or adjusted under 35 U.S.C. 154(b) by 885 days.

(21) Appl. No.: 13/450,321

(22) Filed: Apr. 18, 2012

(65) Prior Publication Data

US 2012/0271205 A1 Oct. 25, 2012

Related U.S. Application Data

(60) Provisional application No. 61/476,721, filed on Apr. 18, 2011.

(51) Int. Cl.
| | | |
|---|---|---|
| *A61H 7/00* | (2006.01) | |
| *A61N 5/06* | (2006.01) | |
| *A61H 23/02* | (2006.01) | |

(52) U.S. Cl.
CPC .... *A61H 23/0254* (2013.01); *A61H 2201/0149* (2013.01); *A61H 2201/1463* (2013.01); *A61H 2201/1695* (2013.01); *A61H 2201/5023* (2013.01); *A61H 2205/086* (2013.01); *A61H 2205/10* (2013.01); *A61H 2207/00* (2013.01); *A61N 2005/064* (2013.01); *A61N 2005/0659* (2013.01); *A61N 2005/0667* (2013.01)

(58) Field of Classification Search
CPC ............ A61H 15/02; A61H 2201/10; A61H 2207/00; A61N 2005/0662; A61N 2005/0663; A61N 2005/0658; A61N 2005/0659; A61N 2005/0643; A61N 2005/0644; A61N 2005/0645; A61N 5/0613; A61N 5/0616; A61N 2005/065; A61N 5/06
USPC ........ 601/15, 18–19, 98; 472/96–97, 99, 102; 297/284.1, 260.2, 258.1, 256.1
See application file for complete search history.

(56) References Cited

U.S. PATENT DOCUMENTS

| 1,183,949 | A | | 5/1916 | Burdick | |
|---|---|---|---|---|---|
| 2,954,771 | A | | 10/1960 | Boyan | |
| 3,062,987 | A | | 11/1962 | Cuffman | |
| 3,298,363 | A | * | 1/1967 | Parkin | ............................ 5/236.1 |
| 3,451,579 | A | | 6/1969 | Bishop | |
| 3,664,333 | A | * | 5/1972 | Hill | .............................. 601/102 |
| 3,824,991 | A | * | 7/1974 | Whitaker | ............... A47C 9/002 |
| | | | | | 601/26 |
| 4,202,326 | A | * | 5/1980 | Van Gerpen | .................... 601/99 |
| 4,679,787 | A | | 7/1987 | Guilbault | |
| 4,947,832 | A | * | 8/1990 | Blitzer | ............... A61H 23/0254 |
| | | | | | 5/109 |
| 5,103,809 | A | * | 4/1992 | DeLuca et al. | ................ 601/135 |

(Continued)

FOREIGN PATENT DOCUMENTS

| CN | 201014318 Y | 3/2008 |
|---|---|---|
| WO | WO2007036002 | 4/2007 |
| WO | WO2011/100972 A1 | 8/2011 |

*Primary Examiner* — Justine Yu  
*Assistant Examiner* — Christopher Miller  
(74) *Attorney, Agent, or Firm* — Bereskin & Parr LLP; Carmela De Luca

(57) ABSTRACT

A light therapy and massaging apparatus includes a base and a chair. A first movement imparting mechanism is provided for displacing the chair assembly relative to the base for displacing a user on the chair assembly in a repeated motion. Infrared light sources are provided in the chair assembly for delivering high energy to the user's body. Paddles extend within openings in the chair assembly for massaging the user's buttocks, the paddles being driven by a second movement imparting mechanism. Protrusions are provided transversally on the chair assembly and opposite the user's legs so as to act on the user's legs when the chair assembly is displaced by the first movement imparting mechanism.

12 Claims, 8 Drawing Sheets

(56) References Cited

U.S. PATENT DOCUMENTS

| | | | |
|---|---|---|---|
| 5,109,558 A * | 5/1992 | Di Blasi | A61G 7/0573 5/236.1 |
| 5,176,130 A * | 1/1993 | Kim | 601/15 |
| 5,441,531 A * | 8/1995 | Zarate | A61N 5/062 604/21 |
| 5,626,555 A * | 5/1997 | Di Blasi | A47C 21/006 5/612 |
| 5,716,331 A * | 2/1998 | Chang | 601/50 |
| 5,743,050 A | 4/1998 | Shibata | |
| 5,904,660 A * | 5/1999 | Kim | 601/108 |
| 5,976,097 A * | 11/1999 | Jensen | 601/24 |
| 6,017,360 A | 1/2000 | Chubb et al. | |
| 6,024,760 A * | 2/2000 | Marchesi | A61N 5/06 607/100 |
| 6,066,087 A | 5/2000 | Tron | |
| 6,149,611 A * | 11/2000 | Chen | 601/22 |
| 6,152,529 A * | 11/2000 | Beason | A47C 3/02 297/260.2 |
| 6,200,282 B1 * | 3/2001 | Furuie et al. | 601/98 |
| 6,254,625 B1 * | 7/2001 | Rosenthal | A61L 2/10 606/10 |
| 6,409,744 B1 | 6/2002 | Marchesi | |
| 6,682,495 B2 * | 1/2004 | Park | 601/98 |
| 7,104,927 B2 * | 9/2006 | Tsai | A63B 69/04 472/95 |
| 7,159,255 B2 * | 1/2007 | Piraino | A47C 23/067 5/238 |
| 7,198,634 B2 * | 4/2007 | Harth et al. | 607/90 |
| 7,341,310 B1 * | 3/2008 | Ross | A47C 3/36 297/344.12 |
| 7,419,475 B2 * | 9/2008 | Ferber et al. | 601/99 |
| 7,670,230 B2 * | 3/2010 | Hsu | A61H 1/001 434/247 |
| 7,713,220 B2 * | 5/2010 | Chen | 601/99 |
| 2003/0055365 A1 * | 3/2003 | Hazard | A47C 3/0255 601/98 |
| 2004/0039428 A1 * | 2/2004 | Williams et al. | 607/91 |
| 2004/0215113 A1 * | 10/2004 | Saringer | A47C 3/02 601/90 |
| 2005/0209538 A1 * | 9/2005 | Lev et al. | 601/15 |
| 2006/0094993 A1 * | 5/2006 | Hazard | 601/98 |
| 2007/0194717 A1 | 8/2007 | Belikov | |
| 2007/0293793 A1 * | 12/2007 | Johnson | 601/15 |
| 2008/0208296 A1 | 8/2008 | Smith et al. | |
| 2008/0312721 A1 | 12/2008 | Lemieux | |
| 2009/0005839 A1 | 1/2009 | Griffith et al. | |
| 2009/0054217 A1 * | 2/2009 | Teeter | 482/144 |
| 2009/0222070 A1 * | 9/2009 | Daffer | 607/91 |
| 2010/0063487 A1 * | 3/2010 | Van Straalen | 606/2 |
| 2011/0199770 A1 | 8/2011 | Pedersen | |
| 2011/0224584 A1 * | 9/2011 | Pryor et al. | 601/15 |
| 2012/0103963 A1 * | 5/2012 | Milfeldt | A47B 31/02 219/218 |
| 2012/0109041 A1 * | 5/2012 | Munz | 604/20 |
| 2012/0265275 A1 | 10/2012 | Kiremitci | |
| 2014/0350644 A1 | 11/2014 | Kiremitci | |

* cited by examiner

FIG-4

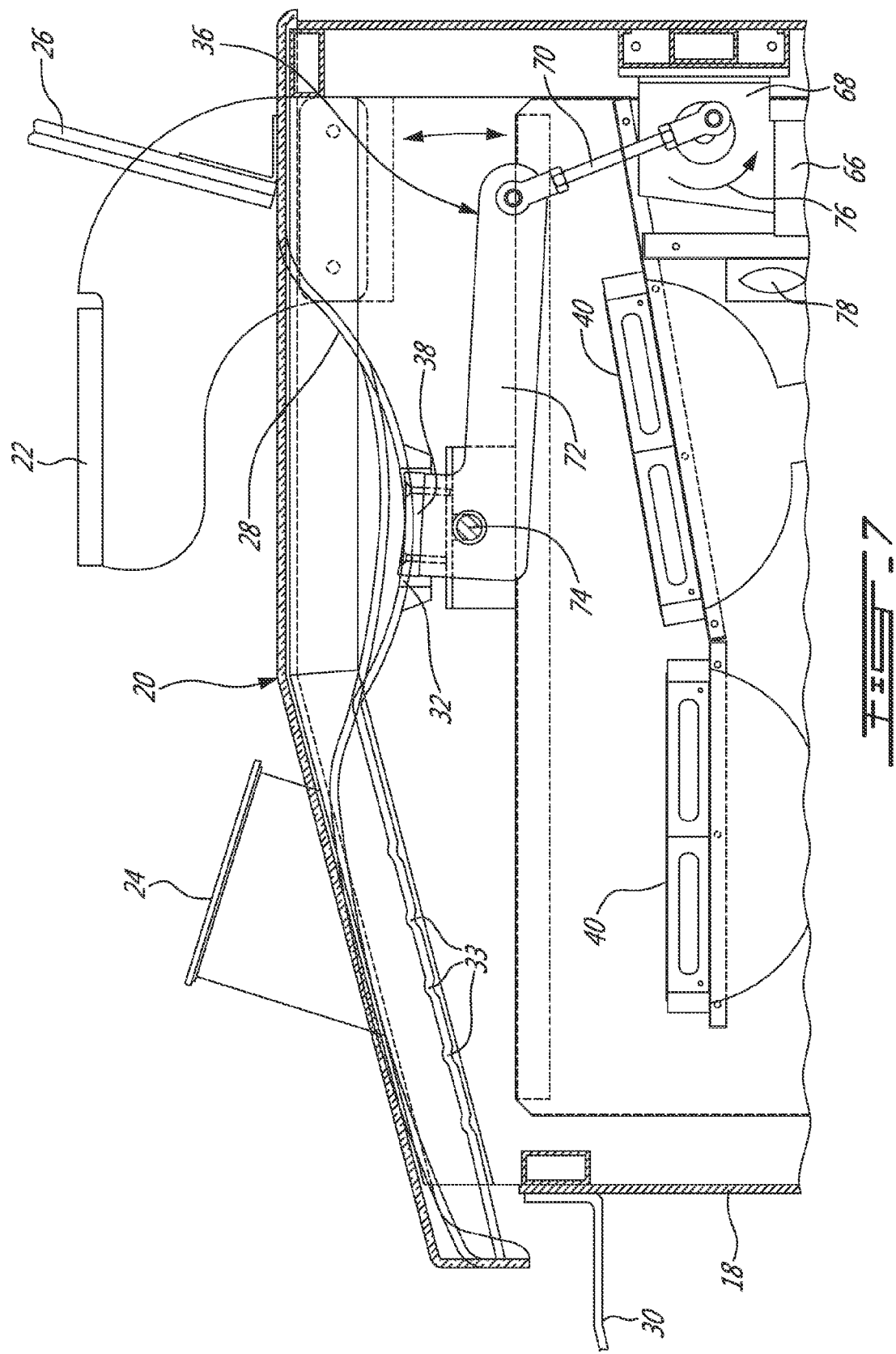

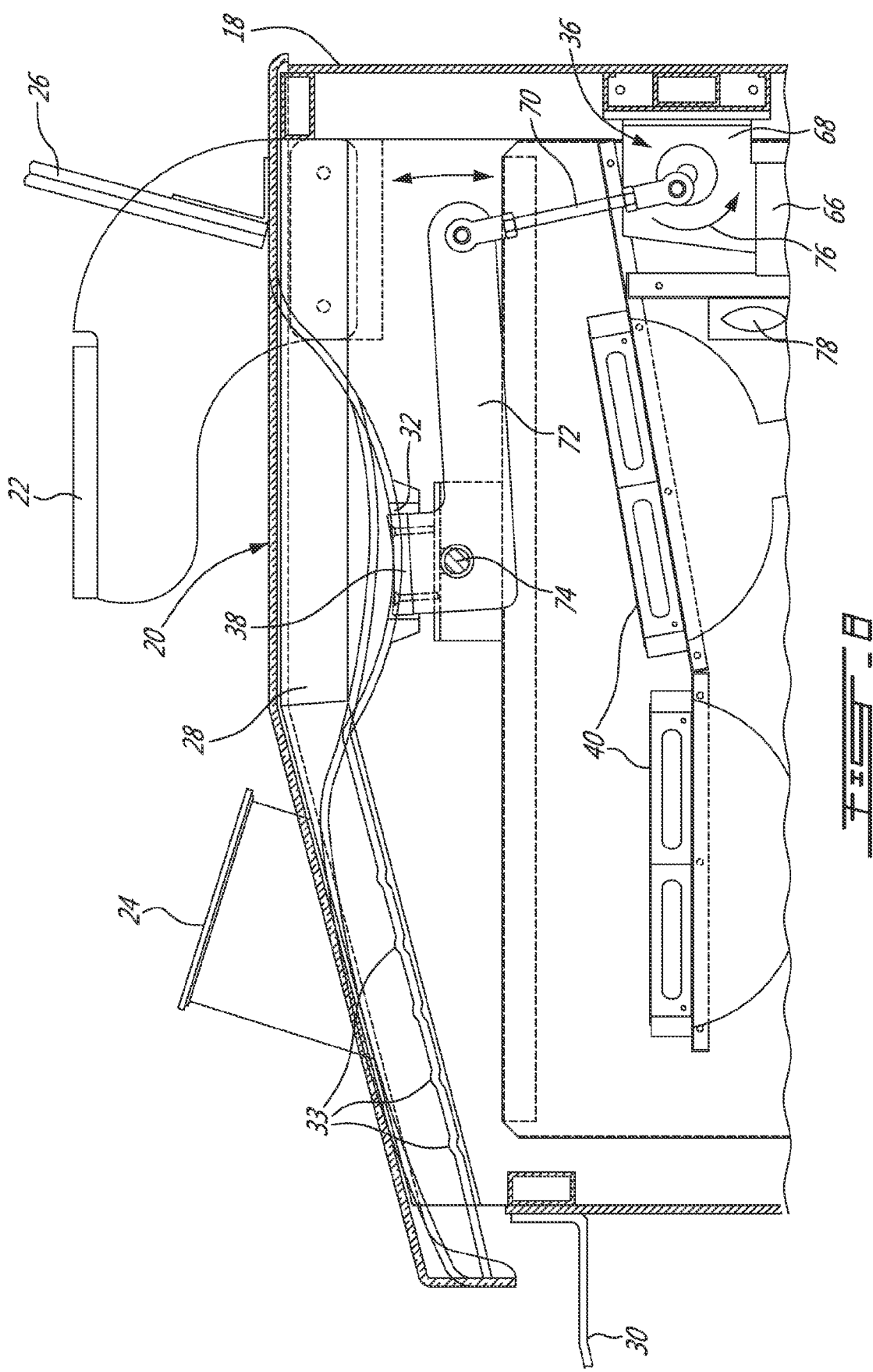

PHOTO LIGHT THERAPY AND MASSAGING APPARATUS

CROSS REFERENCE TO RELATED APPLICATIONS

This Application claims priority on U.S. Provisional Application No. 61/476,721, filed on Apr. 18, 2011, which is herein incorporated by reference.

FIELD OF THE INVENTION

The present invention relates to devices used spas, beauty shops, etc., for the well-being of users.

BACKGROUND OF THE INVENTION

In this age where people are concerned about their well-being and appearances, various methods, products and devices exist for exercising purposes, for improving one's skin texture, etc.

Nevertheless, there is a need in the art for improvements in the area of the well-being of people.

SUMMARY OF THE INVENTION

It is therefore an aim of the present invention to provide a novel apparatus for the well-being of users thereof.

Therefore, in accordance with the present invention, there is provided a light therapy and massaging apparatus, comprising a base and a chair assembly, a first movement imparting mechanism being provided for displacing the chair assembly relative to the base for providing a repeated motion to a user located on the chair assembly, at least one light source being provided for delivering high energy to the user's body.

Also in accordance with the present invention, there is provided a massaging apparatus, comprising a base and a chair assembly, a first movement imparting mechanism being provided for displacing the chair assembly relative to the base for providing a repeated motion to a user located on the chair assembly, at least two paddles being provided for massaging the user, the paddles being driven by a second movement imparting mechanism.

Further in accordance with the present invention, there is provided a massaging apparatus, comprising a base and a chair assembly, a first movement imparting mechanism being provided for displacing the chair assembly relative to the base for providing a repeated motion to a user located on the chair assembly, wherein protrusions are provided transversally on the chair assembly and opposite the user's legs so as to act on the user's legs when the chair assembly is displaced by the first movement imparting mechanism.

Other objects, advantages and features of the present invention will become more apparent upon reading of the following non-restrictive description of embodiments thereof, given by way of example only with reference to the accompanying drawings.

BRIEF DESCRIPTION OF THE DRAWINGS

Reference will now be made to the accompanying drawings, showing by way of illustration an illustrative embodiment of the present invention, and in which:

FIG. 4 is a right-side elevation view of the photo light therapy and massaging apparatus;

FIG. 7 is a right-side elevation view of an upper portion of the photo light therapy and massaging apparatus; and FIG. 8 is a right-side elevation view of the upper portion of the photo light therapy and massaging apparatus, which is similar to FIG. 7 but shows the apparatus in a different position.

DESCRIPTION OF ILLUSTRATIVE EMBODIMENTS OF THE INVENTION

With reference to the drawings, there will now be described a photo light therapy and massaging apparatus A. The apparatus A is to be used in spas, in beauty shops, etc., and also can be used by dermatologists.

Figure 2:
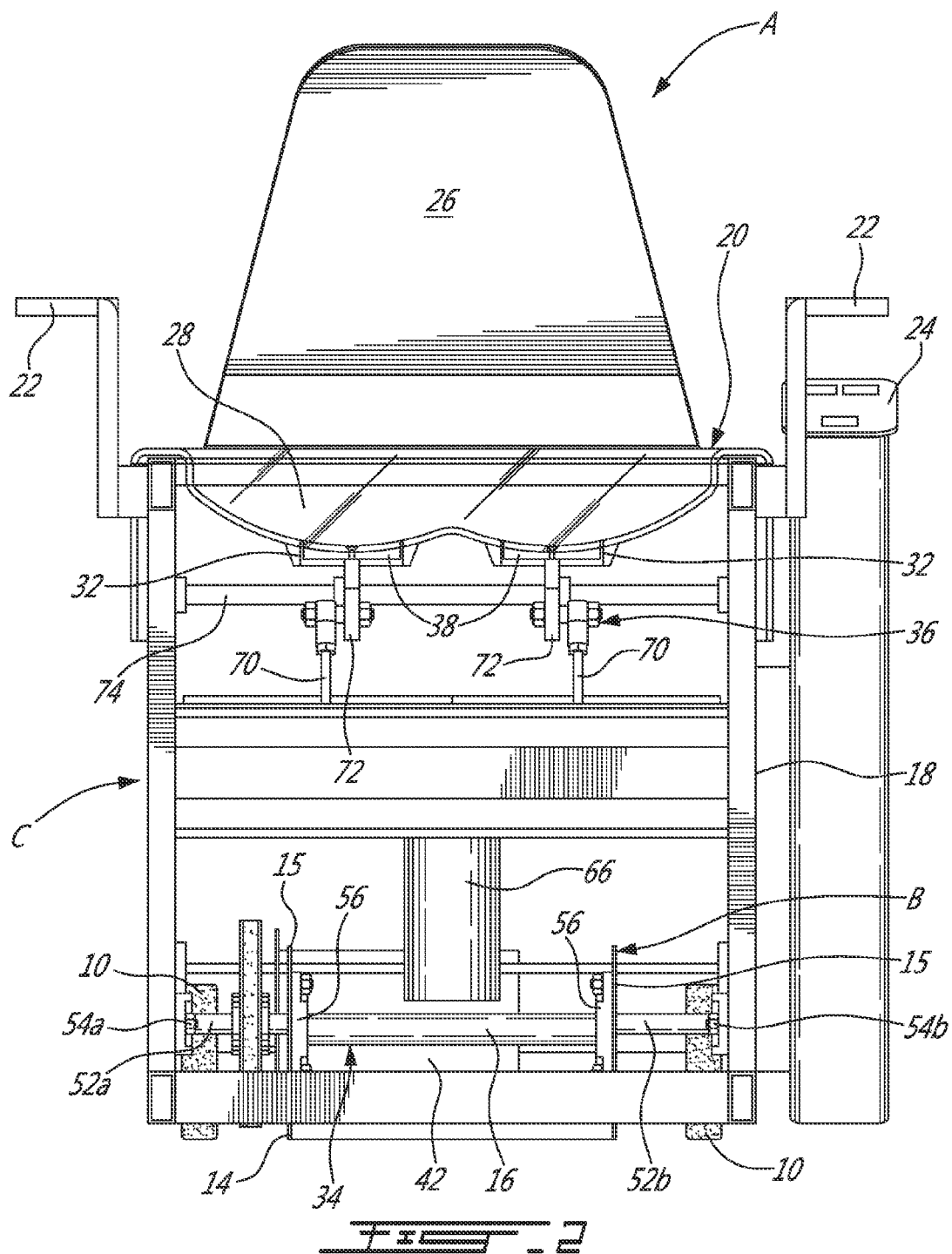
FIG. 2 is a rear view of the photo light therapy and massaging apparatus, with a panel removed to see the inside thereof.
Figure 3:
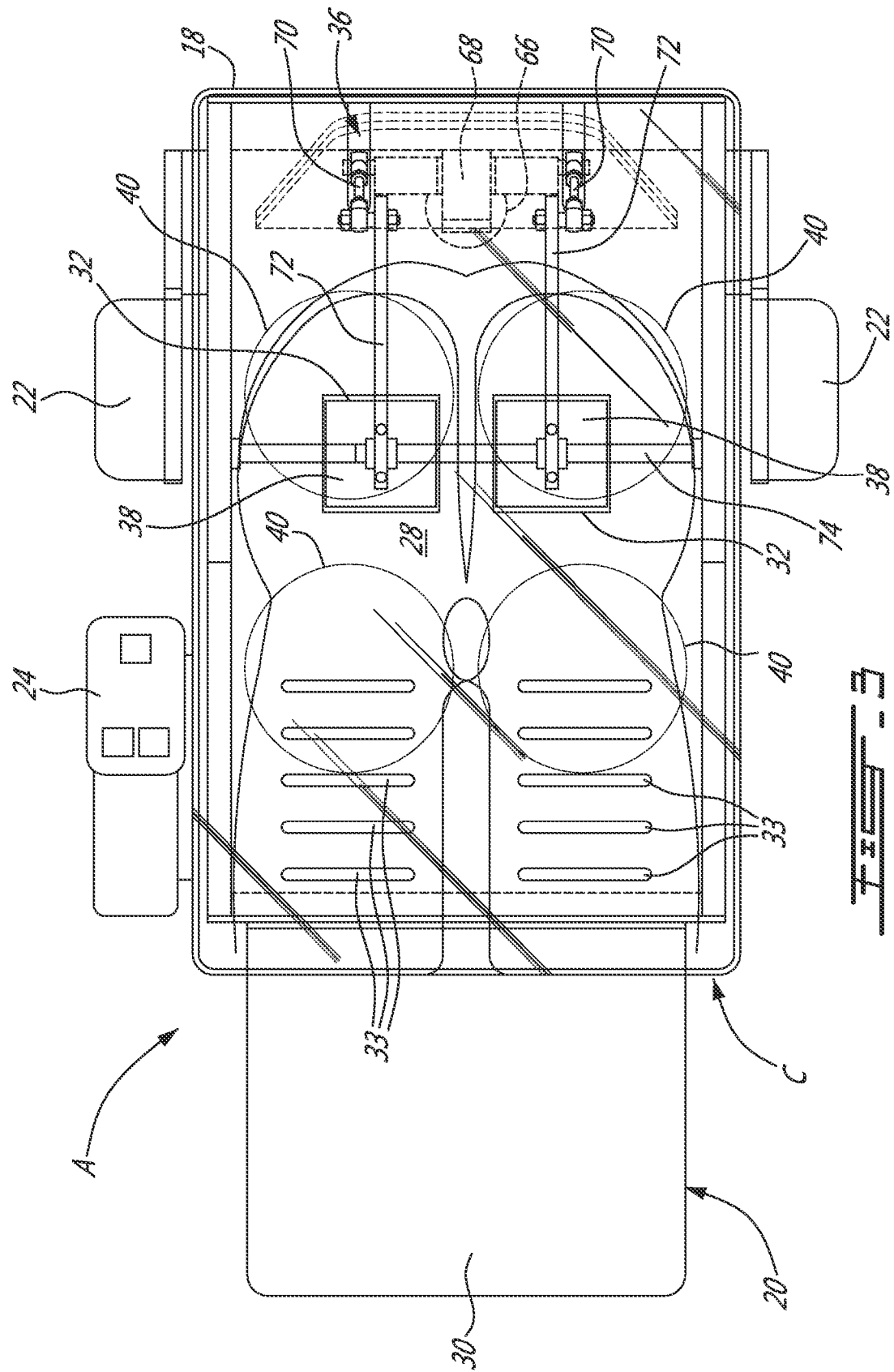
FIG. 3 is a top plan view of the photo light therapy and massaging apparatus.
Figure 4:
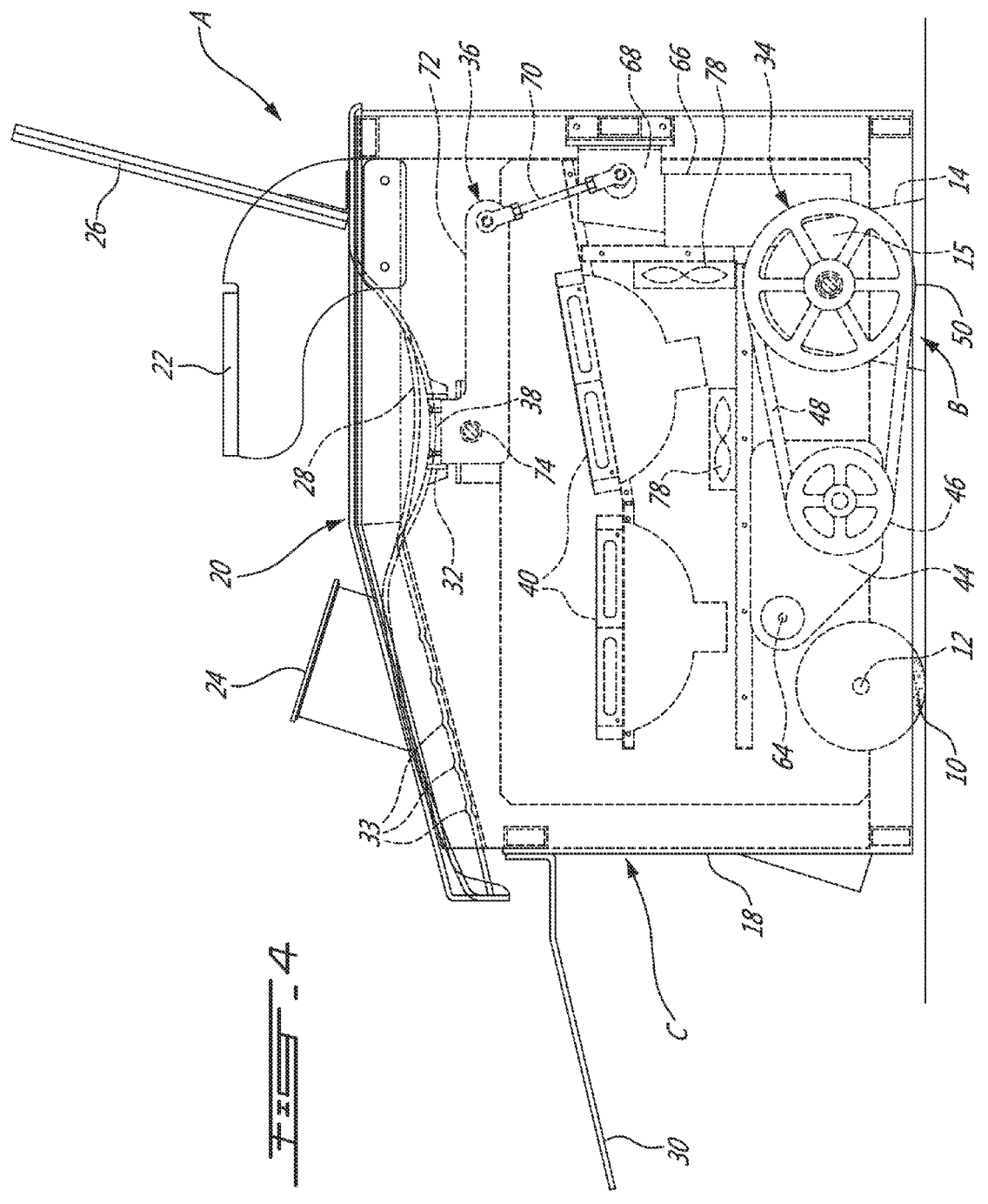

More particularly, the photo light therapy and massaging apparatus A includes a ground-contacting base B, which as seen in FIGS. 2 and 4 includes a pair of front wheels 10, which are mounted on an axle 12. The base B also includes a U-shaped rear support 14 with a shaft 16 being journaled to opposite vertical sections 15 of the rear support 14. A chair assembly C is mounted on the base B for relative movement with respect thereto. Details of the chair assembly C follow hereinbelow.

Figure 1:
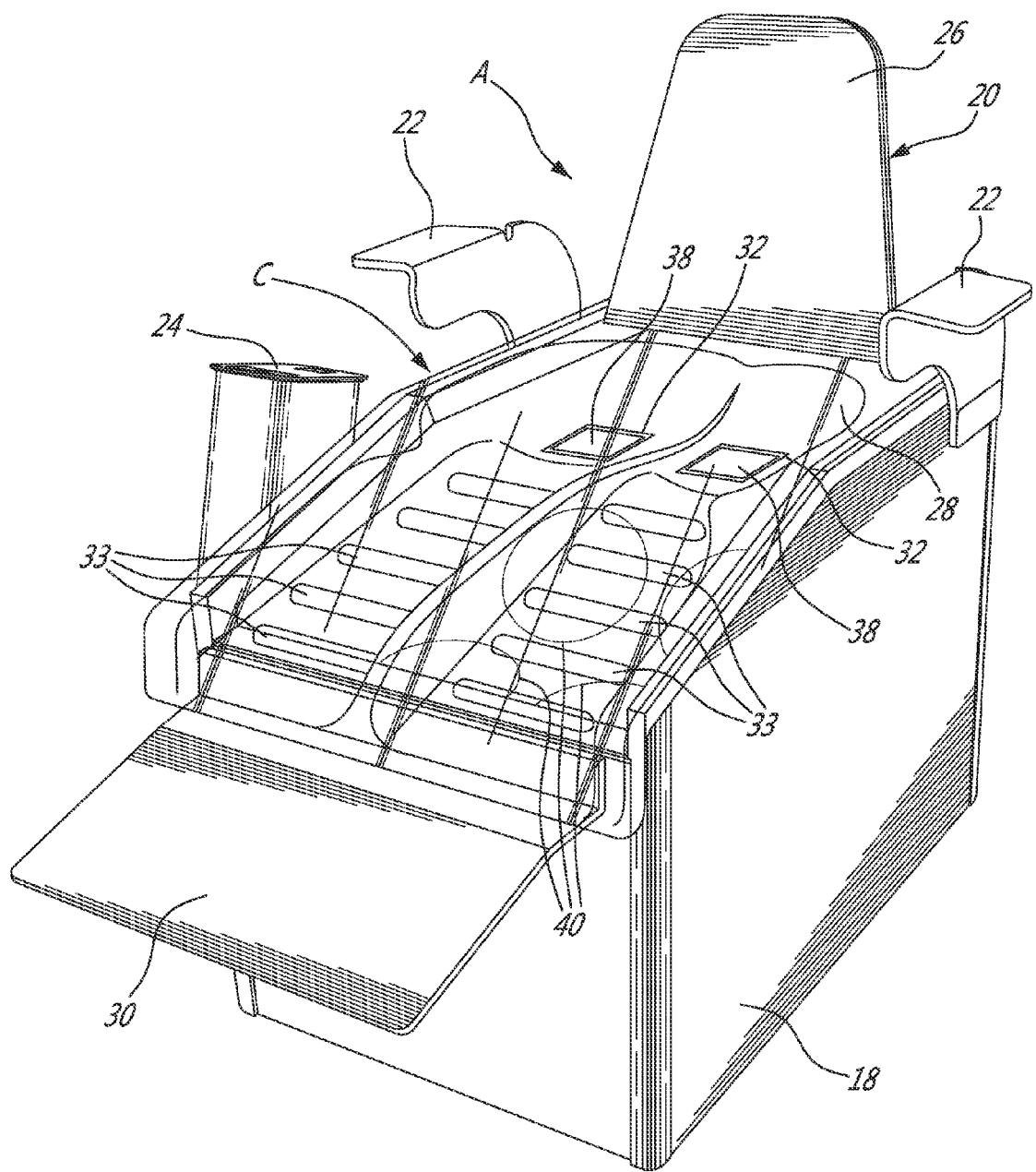
FIG. 1 is a perspective view of a photo light therapy and massaging apparatus in accordance with the present invention.

As seen in FIG. 1, the chair assembly C includes a housing 18 mounted on the base B. A seat 20, side arm rests 22 and panel control 24 are mounted to the housing 18. The seat has a back rest 26, a seat portion 28 and a foot rest 30. The seat portion 28, which is formed, e.g. by moulding, to comfortably receive at least the user's buttocks and thighs, is made of a light-transmitting material and is thus transparent or translucent, for instance made of acrylic. The seat portion 28 defines a pair of openings 32, which are positioned opposite the user's buttocks. The seat portion 28 defines transversely-oriented protrusions or ribs 33, which are located so as to underlie the user's legs.

The apparatus A also includes first and second motorized movement-inducing mechanisms, generally identified by numerals 34 and 36 respectively, which power two different mechanical applications to the user. The first movement-inducing mechanism 34, which is provided at the base of the apparatus A, is adapted to displace the chair assembly C with respect to the base B in such a way as to impart to the user positioned on the seat 20 a wave-like back-and-forth motion consisting of horizontal and vertical components.

The second movement-inducing mechanism 36, which is provided at an upper portion of the apparatus A, is adapted to displace a pair of paddles 38 in an oscillating motion, within the openings 32 defined in the seat portion 28, such that the paddles 38 cyclically act upon the user's buttocks.

Infrared light emitting sources 40, herein in the number of four, such as quartz lamp filter and parabolic reflector combinations, are mounted in the chair assembly C, under the seat 20, and are upwardly directed towards the seat portion 28.

Figure 5:
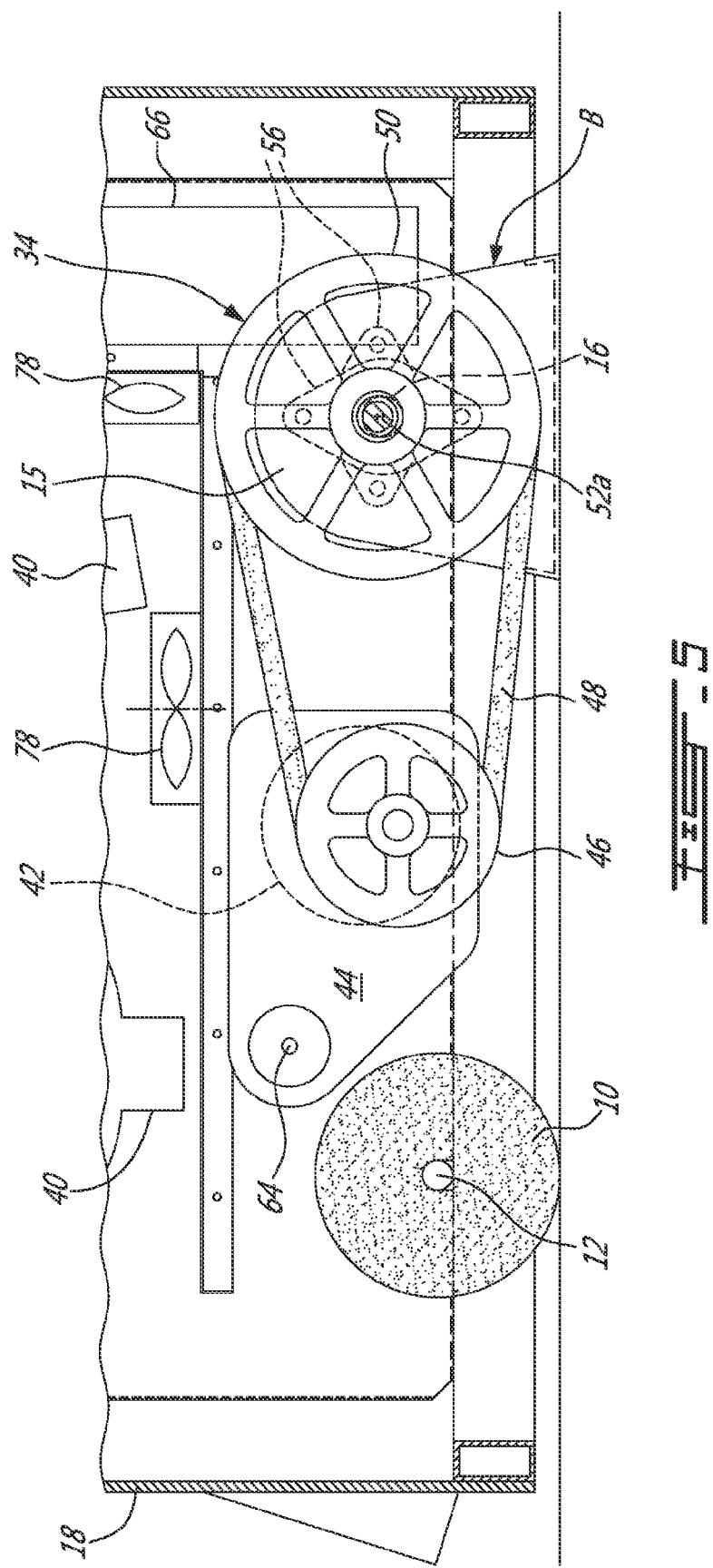
FIG. 5 is a right-side elevation view of a lower portion of the photo light therapy and massaging apparatus.
Figure 6:
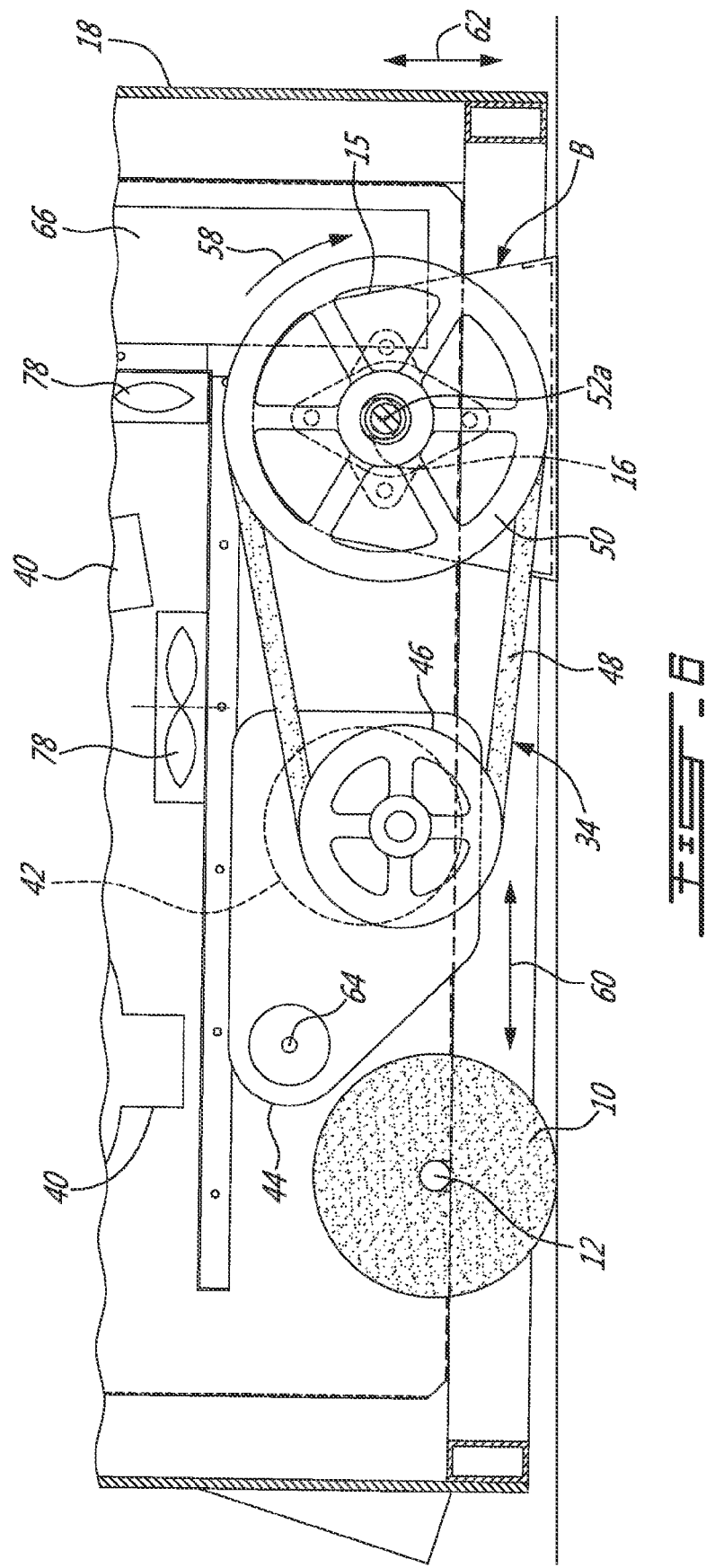
FIG. 6 is a right-side elevation view of the lower portion of the photo light therapy and massaging apparatus, which is similar to FIG. 5 but shows the apparatus in a different position.

The first movement-inducing mechanism 34, which is best seen in FIGS. 2, 5 and 6, includes a variable speed motor (and gearbox) 42 mounted to plate 44, the motor 42 being adapted to rotatably drive a first pulley 46, onto which is engaged a belt 48. A second pulley 50 is mounted to shaft 52a, which is journaled at 54a in the housing 18. A shaft 52b is journaled at 54b to an opposite side of the housing 18. The shafts 52a and 52b are fixed inward ends thereof to the ends of the shaft 16 and eccentrically with respect thereto, as best seen in FIG. 2. Bearings 56 are provided.

Accordingly, rotation of the second pulley 50 (via the motor 42, the first pulley 46 and the belt 48) along arrow 58 (see FIG. 6) causes shaft 52a to rotate and thus also the rotation of the shaft 16 and the shaft 52b. The shaft 16, being journaled in the base B, rotates along a fixed axis, whereby the shaft 16 causes the shafts 52a and 52b, which are mounted to the shaft 16 eccentrically of this axis, to displace along a circular path that lies in a plane perpendicular to the shaft 16. The upper and lower positions of shaft 52a along this path are shown respectively in FIGS. 5 and 6. Since the outward ends of the shafts 52a and 52b are journaled in the housing 18, the circular path followed by the shafts 52a and 52b causes a similar low-amplitude motion of the chair assembly C, horizontal and vertical components of which are shown by arrows 60 and 62, respectively. A pivot is provided at 64.

The second movement-inducing mechanism 36, which is best seen in FIGS. 2, 7 and 8, includes a variable speed motor 66, a gearbox 68, and a pair of connecting rods 70 having their lower ends pivotally mounted eccentrically to the gearbox 68. The upper end of each rod 70 is pivotally mounted to a respective L-shaped arm 72, the two arms 72 being journaled to fixed shaft 74. The paddles 38 are mounted to the upper ends of the L-shaped arms 72. Accordingly, the motor 66 and gearbox 68 cause the lower ends of the connecting rods 70 to displace in a circular path (see arrows 76 in FIGS. 7 and 8), whereby the upper ends of the connecting rods 70 cause the L-shaped arms 72 to pivot about the shaft 74 and thus the paddles 38 to pivot or tilt in a reciprocating motion, two positions of the paddles 38 being shown in FIGS. 7 and 8.

Therefore, from the foregoing, the apparatus A provides a photo light therapy unit, which for instance uses quartz lamp filter and parabolic reflector combinations (e.g. of 500 Watt Plus/each), to deliver a high energy in the safe spectrum so as to treat the thighs, legs, and buttocks of the user while sitting on the formed acrylic seat portion 28. The light-emitting sources 40 transmit the desired infrared spectrum wavelengths, e.g. of 633 nm, 700 nm, 852 nm, to smooth the user's skin, to produce collagen, mechanically massage and drain and gradually reduce cellulite and improve skin condition.

The two paddles 38, for instance sized 3¾" by 3¾", are driven by the second movement-inducing mechanism 36 in a double reverse acting fashion to gently massage the buttock area of the user, thereby aiding in the reduction of the cellulite, Typically, the paddles 38 operate at up to 120 RPM, with the variable speed thereof resulting from the user controlling the speed of the motor 66 via the control panel 24.

The first movement-inducing mechanism 34 displaces the chair assembly C and thus the seat 20 in such a way as that the user receives a real wave motion while sitting on the seat 20 in addition to the infrared light therapy provided by the light-emitting sources 40. The speed of the wave motion depends on the speed of the motor 42, which itself is controlled by the user via the control panel 24. The wave motion is proven to be effective in increasing lymphatic drainage while the user's thighs are rubbing on the transversally defined ribs 33 (which can be for instance ¼" high by ½" wide) formed in the acrylic seat portion 28. This creates a stretching and energizing movement on the skin while it is also bombarded by the light energy.

The system works with the help of light energy to produce collagen, lymphatic drainage and mechanical movement/massage to gradually reduce the cellulite over a number of sessions.

This selected energy is able to reduce pore sizes, improve skin complexion, heal wounds faster, energize the lower epidermis for producing collagen and aid in gradually reducing cellulite.

The infrared energy is able to penetrate approximately ½" in depth to increase the blood flow for even more benefits towards smoother skin.

The apparatus A has the one-piece acrylic seat portion 28 that is moulded to the benefit of the user. Other suitable transparent or translucent materials can also be contemplated for the seat.

The paddles 38 are made for example of infrared-transmitting acrylic sheets and allow the lamps or light-emitting sources 40 to deliver the maximum unobstructed light energy on the buttocks and thighs of the user.

The apparatus A can be manufactured out of moulded plastics or aluminum, metal extrusion and sheet metal formed panels.

The ballasts that are enclosed power the quartz infrared lamps 40 while fans 78 cool the filters, acrylic shield and the components. Also provided is a glass filter specifically made to eliminate the ultraviolet and some of the visible range wavelengths for user's safety.

There is a safety switch that instantly turns the power off to the individual lamps 40 in case that the filter is removed or cracked, broken, or shattered.

There is an exterior clear acrylic shield that protects the users from touching any hot filter and components while transmitting the desired rays.

A totalizer type of hour counter keeps the hours of use to maintain the equipment and replace lamps and other components as scheduled.

A digital timer that can have a maximum time exposure for the user's desire can be used to start and stop the apparatus A and can also be monitored remotely via a daisy chain system.

The present apparatus A advantageously employs simultaneously mechanical massage, high powered safely filtered infrared photo-light energy and mechanical lymphatic drainage, all in one unit that can be safely used by the public.

Although the present invention has been described hereinabove by way of embodiments thereof, it may be modified, without departing from the nature and teachings of the subject invention as described herein.

The invention claimed is:

1. A light therapy and massaging apparatus, comprising:
a base and a chair assembly, a first movement imparting mechanism being provided for displacing the chair assembly relative to the base in a wave-like back-and-forth motion for providing a repeated wave-like back-and-forth motion to a user located on the chair assembly;
at least one light source being configured for delivering energy to the user's thighs, legs and/or buttocks;
wherein the at least one light source is a quartz lamp of 500 Watts and is configured to transmit light at wavelengths of at least one of about 633 nm, about 700 nm and about 852 nm;
wherein the at least one light source is mounted within the chair assembly, a seat portion of the chair assembly being formed of a light-transmitting material and being moulded to receive the user's thighs and/or buttocks, and the light source being configured to transmit light to reach the user's thighs and/or buttocks through the seat portion;

wherein protrusions are provided transversally on the seat portion of the chair assembly defining a plurality of transverse ribs configured to act on the user's legs to create a stretching movement on the user's skin when the chair assembly is displaced in the wave-like back-and-forth motion by the first movement imparting mechanism; and wherein the wave-like back-and-forth motion consists of horizontal and vertical components provided by eccentrically mounted shafts.

2. A light therapy and massaging apparatus as defined in claim 1, wherein the seat portion is made of one of a translucent and transparent material.

3. A light therapy and massaging apparatus as defined in claim 1, wherein at least two paddles are provided for massaging the user's buttocks, the paddles being driven by a second movement imparting mechanism.

4. A light therapy and massaging apparatus as defined in claim 3, wherein the second movement imparting mechanism is adapted to displace the paddles in an alternating motion.

5. A light therapy and massaging apparatus as defined in claim 4, wherein at least two openings are defined in the seat portion of the chair assembly and are configured to be located opposite the user's buttocks, there being at least one paddle extending within each of the openings, the second movement imparting mechanism being adapted to impart a repeated back-and-forth tilting motion to the paddles thereby massaging the buttocks of the user located on the chair assembly.

6. The light therapy and massaging apparatus as defined in claim 3, wherein the at least two paddles permit transmittance of infra-red light.

7. The light therapy and massaging apparatus as defined in claim 3, wherein the at least two paddles are displaced up to a speed of about 120 RPM.

8. A light therapy and massaging apparatus as defined in claim 3, wherein at least two openings are defined in the seat portion of the chair assembly and are configured to be located opposite the user's buttocks, there being at least one paddle extending within each of the openings, the second movement imparting mechanism being adapted to impart a repeated back-and-forth tilting motion to the paddles thereby massaging the buttocks of the user located on the chair assembly.

9. The light therapy and massaging apparatus as defined in claim 1, wherein the at least one light source comprises a quartz lamp filter and parabolic reflector combination.

10. The light therapy and massaging apparatus as defined in claim 9, further comprising a filter configured for eliminating ultraviolet light from the at least one light source.

11. The light therapy and massaging apparatus as defined in claim 1, wherein the energy delivered by the at least one light source is configured to penetrate to approximately ½" in depth of the user's thighs and/or buttocks.

12. The light therapy and massaging apparatus as defined in claim 1, further comprising:

at least two paddles for massaging the user's buttocks, the paddles being driven by a second movement imparting mechanism; and wherein the seat portion is made of one of a translucent and transparent material;

wherein the seat portion of the chair assembly defines a plurality of transverse ribs configured to be opposite the user's legs so as to act on the user's legs when the chair assembly is displaced by the first movement imparting mechanism;

wherein the at least two paddles permit transmittance of infra-red light; and wherein at least two openings are defined in the seat portion of the chair assembly and are configured to be located opposite the user's buttocks, there being at least one paddle of said paddles extending within each of the openings, the second movement imparting mechanism being adapted to impart a repeated back-and-forth tilting motion to the paddles thereby massaging the buttocks of the user located on the chair assembly.

* * * * *